(12) United States Patent
Lee et al.

(10) Patent No.: US 7,999,067 B2
(45) Date of Patent: *Aug. 16, 2011

(54) PROTEASE RESISTANT MUTANTS OF STROMAL CELL DERIVED FACTOR-1 IN THE REPAIR OF TISSUE DAMAGE

(75) Inventors: Richard T. Lee, Weston, MA (US); Vincent Segers, Cambridge, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/683,253

(22) Filed: Jan. 6, 2010

(65) Prior Publication Data

US 2010/0184950 A1    Jul. 22, 2010

Related U.S. Application Data

(63) Continuation of application No. 11/976,032, filed on Oct. 19, 2007, now Pat. No. 7,696,309.

(60) Provisional application No. 60/929,353, filed on Jun. 22, 2007, provisional application No. 60/853,441, filed on Oct. 23, 2006.

(51) Int. Cl.
*A61K 38/16* (2006.01)
*A61K 38/00* (2006.01)

(52) U.S. Cl. ............. 530/300; 530/345; 530/402; 514/2

(58) Field of Classification Search ........................ None
See application file for complete search history.

(56) References Cited

U.S. PATENT DOCUMENTS

| | | | |
|---|---|---|---|
| 5,563,048 A | 10/1996 | Honjo et al. | |
| 5,670,483 A | 9/1997 | Zhang | |
| 5,756,084 A | 5/1998 | Honjo et al. | |
| 6,214,540 B1 | 4/2001 | DiVico et al. | |
| 6,548,630 B1 | 4/2003 | Zhang | |
| 6,852,508 B1 | 2/2005 | Hermann et al. | |
| 6,875,738 B1 | 4/2005 | Clark-Lewis et al. | |
| 6,946,445 B1 | 9/2005 | Clark-Lewis et al. | |
| 7,354,899 B2 | 4/2008 | Clark-Lewis et al. | |
| 7,378,098 B2 | 5/2008 | Tudan et al. | |
| 7,435,718 B2 | 10/2008 | Tudan et al. | |
| 7,547,674 B2 | 6/2009 | Anversa et al. | |
| 7,662,392 B2 | 2/2010 | Itescu | |
| 2002/0094327 A1 | 7/2002 | Petersen | |
| 2002/0107195 A1 | 8/2002 | Gupta | |
| 2002/0107196 A1 | 8/2002 | Gupta | |
| 2002/0111290 A1 | 8/2002 | Homey et al. | |
| 2002/0156023 A1 | 10/2002 | Walling et al. | |
| 2002/0165123 A1 | 11/2002 | Tudan et al. | |
| 2003/0199464 A1 | 10/2003 | Itescu | |
| 2003/0215792 A1 | 11/2003 | Muller et al. | |
| 2004/0037811 A1 | 2/2004 | Penn et al. | |
| 2004/0247564 A1 | 12/2004 | Itescu | |
| 2005/0020528 A1 | 1/2005 | Herrmann et al. | |
| 2005/0059584 A1* | 3/2005 | Merzouk et al. | 514/12 |
| 2005/0142101 A1 | 6/2005 | Forssmann et al. | |
| 2005/0271639 A1 | 12/2005 | Penn et al. | |
| 2006/0088510 A1 | 4/2006 | Lee et al. | |
| 2006/0110374 A1 | 5/2006 | Czeiger et al. | |
| 2006/0148703 A1 | 7/2006 | Lee et al. | |
| 2007/0060512 A1 | 3/2007 | Sadeghi et al. | |
| 2007/0203062 A1 | 8/2007 | Ellis-Behnke et al. | |
| 2007/0224171 A1 | 9/2007 | Penn et al. | |
| 2007/0258943 A1 | 11/2007 | Penn et al. | |
| 2008/0253996 A1 | 10/2008 | Boschert et al. | |

FOREIGN PATENT DOCUMENTS

| | | |
|---|---|---|
| WO | 02/38172 A2 | 5/2002 |
| WO | 2004/017978 A1 | 3/2004 |
| WO | 2004/094465 A2 | 11/2004 |
| WO | 2006/074464 A2 | 7/2006 |
| WO | 2006/124013 A2 | 11/2006 |
| WO | 2007/079460 A2 | 7/2007 |

OTHER PUBLICATIONS

Heveker et al. (2001) Pharmacological properties of peptides derived from stromal cell-derived factor 1: study on human polymorphonuclear cells, Mol. Pharmacol., vol. 59, No. 6, pp. 1418-1425.*

Askari, et al., "Effect of Stromal-Cell-Derived factor 1 on stem-cell homing and tissue regeneration in ischemic cardiomyopathy," Lancet 362:697-703 (Aug. 2003).

Carr, A.N. et al., Cardiovascular research, 69:925-935 (2006). "Efficacy of systemic administration of SDF-1 in a model of vascular insufficiency: Support for an endothelium-dependent mechanism."

Chen, et al., "Site Specific Labeling of Cell Surface Proteins With Biophysical Probes Using Biotin Ligase," Nature Methodr 2(2):99-104 (Feb. 2005).

Cosset, F. L et al., Journal of Virology, 69(12):7430-7436 (1995). "High-titer packaging cells producing recombinant retroviruses resistant to human serum."

Crump, et al., "Solution Structure and Basis for Functional Activity of Stromal Cell-Derived Factor-I; Dissociation of CXCR4 Activation from binding and Inhibition of HIV-I," EMBO J. 16:6996-7007 (1997).

Davis, et al., "Local Myocardial Insulin Like growth Factor 1 (IGF-I)delivery with Biotinylated Peptide Nanofibers Improves Cell Therapy for Myocardial Infarction," Proc. Nat'l Acad. Sci. USA 103(21): 8155-8160 (May 2006).

Elambdough, I. et al., Journal of Moiecular and Cellular Cardiology, 42:792-803 (2007). Ex vivo delivered stromal cell-derived factor-1alpha promotes stem cell homing and induces angiomyogenesis in the infarcted mycardium.

Gallagher, et al., "Diabetic Impairments in NO-Mediated Endothelial Progenitor Cell Mobiiization and Homing are Reversed by Hyperoxia and SDF-1A," J. Clin. Invest. 117(5):1249-1259 (May 2007).

(Continued)

*Primary Examiner* — Anand Desai
*Assistant Examiner* — Samuel Liu
(74) *Attorney, Agent, or Firm* — Nixon Peabody LLP

(57) ABSTRACT

The present invention is directed stromal cell derived factor-1 peptides that have been mutated to make them resistant to digestion by the proteases dipeptidyl peptidase IV (DPPIV) and matrix metalloproteinase-2 (MMP-2) but which maintain the ability of native SDF-1 to attract T cells. The mutants may be attached to membranes formed by self-assembling peptides and then implanted at sites of tissue damage to help promote repair.

15 Claims, No Drawings

OTHER PUBLICATIONS

Heveker, et al. (2001) Pharmacological properties of peptides derived from stromal cell-derived factor 1: study on human polymorphonuclear cells, Mol. Pharmacol., vol. 59, No. 6, pp. 1418-1425.

Hiasa, K. et al., Circulation, 109:2454-2461 (2004). "Gene transfer of stromal cell-derived factor-1alpha enhances ischemic vasculogenesis and angiogenesis via vascular endothelial growth factor/endothelial nitric oxide synthase-related pathway.".

Hsieh, el at., "Controlled Delivery of PDGF-BB for Myocardial Protection Using Injectable Self-Assembling Peptide Nanofibers," J. Clin. Invest. 116(1):237-248 (Jan. 2006).

Koch, K.C. et al, Basic Res Cardiol, 100:1-9 (2005). "Effect of catheter-based transendocardial delivery of stromal cell-derived factor 1alpha on left ventricular function and perfusion in a porcine model of myocardial infarction."

Lapidot, et al.,"How Do Stem Cells Find Their Way Home?" Blood 106(6)1901-1910 (Sep. 2005).

Loetscher et al. (1998) N-terminal peptides of stromal cell-derived factor-1 with CXC chemokine receptor 4 agonist and antagonist activities, J. Biol. Chem., vol. 213, No. 35, pp. 22279-22283.

Medical Technology 3-DM Inc. Products, Introduction, Puramatrix [cited Aug. 4.2009] Access: http//www.puramatix.com/pr01,html.

Mirshahi et al. (2000) SDF-1 activity on microvascular endothelial cells; consequences on angiogenesis in in vitro and in vivo models, Thromb. Res., vol. 99, No. 6, pp. 587-594.

Nagasawa, et al., "Defects of B-Cell Lymphopoiesis and Bone-Marrow Myelopoiesis in Mice Lacking the CXC Chemokine PGSF/SDF-1," Nature 382:635-638 (Aug. 1996).

Netzel-Arnett, S. et al., Biochemistry, 32:6427-6432 (1993). Comparative sequence specificit es of human 72-and 92-kDa gelatinases (Type IV collagenases) ans PUMP (Matrilysin).

Penn, et al., "Role of Stem Cell Homing in Myocardial Regeneration," Int. J. Cardiol. 95(Suppl. I): S23-S25 (2004).

Pillarisetti, et al., "Cloning and relative expression Analysis of rat Stromal Cell Derived Factor-1 (SDF-1)1: SDF-1 alpha mRNA is Selectively Induced in Rat Model of Myocardial Infarction," Inflammation 25(5):293-300 (Oct. 2001).

Sasaki, T. et al., Pediatrics International, 49:966-971 (2007). "Stromal cell-derived factor-1alpha improves infarcted heart function through angiogenesis in mice.".

Saxena, E. et al., Circulation 117:2224-2231 (2008). "Stomal cell-derived factor-1 alpha is cardioprotective after myocardial infarction.".

Segers et al. (Oct. 2007) Local delivery of protease-resistant stromal cell derived factor-1 for stem cell recruitment after myocardial infarction, Circulation, vol. 116, No. 15, pp. 1683-1692.

Shioda, T. et al., Proc. Natl. Acad. Sci. USA, 95:63331-6336 (1998). "Anti-HIV-1 and chemotactic activities of human stromal cell-derived factor 1alpha (SDF-lalpha) and SDF-1beta are abolished by CD26/dipeptidyl peptidase IV-mediated cleavage."

Yamaguchi, J. et al., Circulation, 107:1322-1328 (2003). "Stromal cell-derivved factor-1 effects on ex vivo expanded endothelial progenitor cell recruitment of ischemic neovascularization."

Zhang. G. et al., Tissue Engineering, 13(8):2063-2071 (2007). "Controlled release of stromal cell-derived factor-1alpha in situ increases C-kit+cell homing to the infarcted heart."

Zhong, et al. (2004) Small peptide analogs to stromal derived factor-1 enhance chemotactic migration of human and mouse hematopoletic cells, Exp. Hematot, vol. 32, No. 5, pp. 470-475.

Zou et al., "Function of the Chemokine Receptor CXCR4 in Haematopoiesis and Cerebellar development," Nature 393:595-599 (Jun. 1998).

De La Luz Sierra Maria at al. "Differential processing of stromal-derived factor-1alpha and stromal-derived factor-1beta explains functional diversity," Blood, American Society of Hematology, 103(7):2452-2459 (2004).

Kryczek Ilona at al. "Stroma-derived factor (SDF-1/CXCL12) and human tumor pathogenesis," American Journal of Physiology, Cell Physiology, American Physiological Society, 292(3):C987-C995 (2007).

Lambier, A.M. at al. "Kinetic investigation of chemokine truncation by CD26/dipeptidyl peptidase IV reveals a striking selectivity within the chemokine family," The Journal of Biological Chemistry 276(32):29839-29845 (2001).

Ohnishi Yukano et al. "Identification and expression of recombinant native SDF-1alpha with additional mutagenesis studies: An attempt at more comprehensive interpretation of accumulated structure-activity relationship data," Journal of Interferon and Cytokine Research, 20(8):691-700 (2000).

Rosenblum J.S. at al., "Prolyl peptidases: A serine protease subfamily with high potential for drug discovery," Current Opinion in Chemical Biology, Current Biology Ltd., London, 7(4):496-504 (2003).

Tan Y. et al. "Cloning and characterizing mutated human stromal cell-derived factor-1 (SDF-1): C-terminal alpha-helix of SDF-1alpha plays a critical role in CXCR4 activation and signaling, but not in CXCR4 binding affinity," Experimental Hematology, Elsevier Inc., 34(11):1553-1562 (2006).

Yu, L. et al. "Identification and expression of novel isoforms of human stromal cell-derived factor 1," Gene, Elsevier, Amsterdam, NL Lnkd-Doi:10.1016/J Gene 374(7)174-179 (2006).

Valenzuela-Fernandez Agustin et al. "Leukocyte elastase negatively regulates Stromal cell-derived factor-1 (SDF-1) and CXCR4," The Journal of Biological Chemistry, 277(18)15677-15689 (2002).

* cited by examiner

PROTEASE RESISTANT MUTANTS OF STROMAL CELL DERIVED FACTOR-1 IN THE REPAIR OF TISSUE DAMAGE

CROSS REFERENCE TO RELATED APPLICATIONS

This application is a continuation under 35 U.S.C. 120, 121, or 365(c) of U.S. patent application Ser. No. 11/976,032 filed Oct. 19, 2007, which claims priority to and benefit under 35 U.S.C. 119(e) of U.S. Provisional Application Nos. 60/929,353 filed on Jun. 22, 2007 and 60/853,441 filed on Oct. 23, 2006. The contents of each of these applications is hereby incorporated by reference in its entirety.

FIELD OF THE INVENTION

The present invention is directed to stromal cell derived factor-1 (SDF-1) peptides that have been mutated in a manner that preserves their ability to attract cells but which makes them resistant to inactivation by proteases, particularly matrix metalloproteinase-2 (MMP-2) and/or dipeptidyl peptidase IV (DPPIV/CD26). When delivered to damaged tissue, these mutants promote tissue repair. The peptides should also be useful in the treatment of many conditions, including ulcers in the gastrointestinal tract or elsewhere, wounds resulting from accident, surgery or disease; and cardiac tissue damaged as the result of a myocardial infarction. The peptides should also be useful in treating diabetic patients to make them less susceptible to damage caused by wounds, ulcers or lesions. In an especially preferred embodiment, the mutated forms of SDF-1 are delivered to damaged tissue using a membrane formed by self-assembling peptides.

BACKGROUND OF THE INVENTION

Stromal cell derived factor-1 (SDF-1, or CXCL12) is a 68 amino acid member of the chemokine family which attracts resting T-lymphocytes, monocytes and CD34+ stem cells. It is commonly found in two different forms SDF-1α and SDF-1β which are the result of differential mRNA splicing (U.S. Pat. No. 5,563,048). These forms are essentially the same except that SDF-1β is extended by four amino acids (-Arg-Phe-Lys-Met) at the C terminus. Both forms of SDF-1 are initially made with a signal peptide, 21 amino acids in length, that is cleaved to make the active peptide (U.S. Pat. No. 5,563,048). For the purposes of the present invention, it will be understood that the term "SDF-1" refers to the active form of the peptide, i.e., after cleavage of the signal peptide, and encompasses both SDF-1α and SDF-1β.

It has also been shown that the full length, 68 amino acid, SDF-1 sequence is not needed for activity. Peptides that have at least the first eight N-terminal residues of SDF-1 maintain the receptor binding and bioactivity of the full peptide, albeit at a reduced potency. For example, SDF-1, 1-8, 1-9, 1-9 dimer, and 1-17 induce intracellular calcium and chemotaxis in T lymphocytes and CEM cells and bind to CXC chemokine receptor 4 (CXCR4). However, native SDF-1 has half-maximal chemoattractant activity at 5 nM, whereas the 1-9 dimer requires 500 nM and is therefore 100-fold less potent. The 1-17 and a 1-9 monomer analogs are 400- and 3600-fold, respectively, less potent than SDF-1. SDF-1 variants with C-terminal cyclization have been described that have a higher CXCR4 receptor binding affinity and cyclization of this type may, if desired, be used in connection with the peptides described herein. For the purposes of the present invention, the term SDF-1 will include forms of the peptide that have been truncated at the C terminal end but which maintain SDF-1 biological activity, i.e., which are chemotactic for T lymphocytes and CEM cells and which bind to CXC chemokine receptor 4 (CXCR4). At a minimum, these truncated forms include the first eight amino acids at the N-terminal end of the peptide.

SDF-1 plays a key-role in the homing of hematopoietic stem cells to bone marrow during embryonic development (Nagasawa, et al., *Nature* 382:635-638 (1996); Zou, et al., *Nature* 393:595-599 (1998)) and after stem cell transplantation (Lapidot, et al., *Blood* 106:1901-1910 (2005)). In addition to its role in stem cell homing, SDF-1 is also important in cardiogenesis and vasculogenesis. SDF-1 deficient mice die perinatally and have defects in cardiac ventricular septal formation, bone marrow hematopoiesis and organ-specific vasculogenesis (Nagasawa, et al., *Nature* 382:635-638 (1996); Zou, et al., *Nature* 393:595-599 (1998)). It has also been reported that abnormally low levels of SDF-1 are at least partially responsible for the impaired wound healing associated with diabetic patients and that impairment can be reversed by the administration of this cytokine at the site of tissue damage (Gallagher, et al., *J. Clin. Invest.* 117:1249-1259 (2007)).

In the normal adult heart, SDF-1 is expressed constitutively, but expression is upregulated within days after myocardial infarction (Pillarisetti, et al., *Inflammation* 25:293-300 (2001)). Askari et al. increased SDF-1 expression 8 weeks after myocardial infarction by intramyocardial transplantation of stably transfected cardiac fibroblasts overexpressing SDF-1 in combination with G-CSF therapy (*Lancet* 362:697-703 (2003)). This was associated with higher numbers of bone marrow stem cells (c-Kit or CD34 positive) and endothelial cells in the heart and resulted in an increase of vascular density and an improvement of left ventricular function. These studies suggest that the insufficiency of the naturally-occurring myocardial repair process may be in part due to inadequate SDF-1 availability. Hence, the delivery of SDF-1 in a controlled manner after myocardial infarction may attract more progenitor cells and thereby promote tissue repair (Penn, et al., *Int. J. Cardiol.* 95(*Suppl.* 1):S23-S25 (2004)). Apart from this, the administration of SDF-1 may be used to improve the healing of wounds or ulcers in patients, especially those with diabetes.

One way that may be used for the sustained delivery of drugs at a site of tissue damage is through the use of biologically compatible membranes. Certain peptides are capable of self-assembly when incubated in the presence of a low concentration of monovalent metal cation (U.S. Pat. No. 5,670,483; U.S. Pat. No. 6,548,630). Assembly results in the formation of a gel-like membrane that is non-toxic, non-immunogenic and relatively stable to proteases. Once formed, membranes are stable in serum, aqueous solutions and cell culture medium. They can be made under sterile conditions, are capable of supporting the growth of cells and are slowly digested when implanted in an animal's body. These characteristics make the membranes well suited as devices for the delivery of therapeutic agents (US 20060148703 and 20060088510).

SUMMARY OF THE INVENTION

The present invention is based, in part, on experiments that had as their hypothesis that the beneficial effect of stromal cell derived factor-1 (SDF-1) in the recovery of damaged cardiac tissue is limited by high concentrations of the protease matrix metalloproteinase-2 (MMP-2) present in such tissue. More specifically, it was proposed that the MMP-2 cleaves SDF-1 and thereby eliminates its ability to attract progenitor cells to the site of tissue damage.

In order to test this hypothesis, the inventors developed mutated forms of SDF-1 that retain their ability to attract T cells but which are resistant to MMP-2 digestion. The mSDF-1 peptides were attached to a specially designed membrane formed by self-assembling peptides and then tested in an animal model of cardiac damage. It was found that mSDF-1 attached to membranes and implanted into the myocardium of test animals improved cardiac recovery to a greater extent than either SDF-1 or mSDF-1 that was not attached to membranes.

In addition, the inventors found that truncated forms of SDF-1 maintain bioactivity and, as with the full length peptide, mutations in the fourth or fifth amino acids protect the peptide from protease digestion.

In its first aspect, the invention is directed to mutant forms of SDF-1 (mSDF-1) which are characterized by a change in the fourth and/or the fifth amino acid from the N-terminus of unmutated SDF-1 (KPVSLSYRCPCRFFESHVARANVK-HLKILNTPNCALQIVARLKNNNRQVCIDPKLKWIQE-YLEKALNK (SEQ ID NO:52)). Thus, the fourth amino acid is changed to an amino acid other than S and/or the fifth amino acid is changed to an amino acid other than L. As discussed above, truncated forms of the full length SDF-1 peptide maintain biological activity provided that the first eight amino acids (highlighted in the sequence shown above) are present and these truncated forms may also be made protease resistant by mutating the fourth and/or fifth position. The invention includes these biologically active truncated mutants as well. Put another way, the invention includes peptides comprising the amino acid sequence of at least amino acids 1-8 of SEQ ID NO:52, which are optionally extended at the C terminus by all or any portion of the remaining sequence of SEQ ID NO:52, shown as amino acids 9-68. In all cases, the peptide will have a sequence corresponding to that given in SEQ ID NO:52 except that there will be a proteinogenic amino acid other than S at position 4 and/or a proteinogenic amino other than L at position 5.

For the purposes of the present invention, all peptide sequences are written from the N terminus (far left) to the C terminus (far right) and unless otherwise indicated, all amino acids are "proteinogenic" amino acids, i.e., they are the L-isomers of: alanine (A); arginine (R); asparagine (N); aspartic acid (D); cysteine (C); glutamic acid (E); glutamine (Q); glycine (G); histidine (H); isoleucine (I); leucine (L); lysine (K); methionine (M); phenylalanine (F); proline (P); serine (S); threonine (T); tryptophan (W); tyrosine (Y); or valine (V). Mutant SDF-1 peptides may be abbreviated herein as "mSDF-1," "mSDF" or SDF(NqN') where N is the one letter designation of the amino acid originally present, q is its position from the N terminus of the peptide and N' is the amino acid that has replaced N. It will also be understood that, although SEQ ID NO:52 shows the intact full length sequence of SDF-1α, this sequence may be extended at the C terminus by up to four more amino acids, in particular with the sequence—R-F-K-M. Thus, the invention includes mutant forms of both SDF-1α and SDF-1β (see U.S. Pat. No. 5,563, 048). In some instances, peptides that have been mutated by the addition of amino acids at the N terminus are abbreviated as "Xp-R" where X is a proteinogenic amino acid, p is an integer and R is the peptide prior to extension. It will also be understood that, unless otherwise indicated, all pharmaceutically acceptable forms of peptides may be used, including all pharmaceutically acceptable salts.

The mSDF-1 peptides must maintain chemoattractant activity with a sensitivity (as determined by, e.g., the effective concentration needed to obtain 50% of maximal response in the assays of Jurkat T cell migration described herein) of at least $\frac{1}{10}$ the sensitivity of unmutated SDF-1. In addition, the mSDF-1 peptides must be resistant to loss of this chemoattractant activity due to cleavage by matrix metalloproteinase-2 (MMP-2). Preferably the rate of inactivation of mSDF-1 is less than $\frac{1}{2}$ (and more preferably, less than $\frac{1}{4}$ or $\frac{1}{10}$) the rate of inactivation of SDF-1.

In one embodiment, the mSDF-1 peptide has the sequence: KPVXLSYRC PCRFFESHVARANVKHLKILNTPNCAL-QIVARLKNNNRQVCI DPKLKWIQEYLEKALNK (SEQ ID NO:53) where X is any of the 20 proteinogenic amino acids except S. The most preferred of these peptides is SDF (S4V) which has the sequence: KPVVLSYRCPCRFFESH-VARANVKHLKILNTPNC ALQIVARLKNNNRQVCIDP-KLKWIQEYLEKALNK (SEQ ID NO:54). SEQ ID 53 and 54 show the full sequence of SDF-1 peptides. However, it will be understood that truncated versions of the peptides will maintain activity as long as the first eight N-terminus amino acids are present. These are also part of the invention and may be made protease resistant by mutating the amino acids at positions 4 and/or 5.

In another embodiment, the mSDF-1 peptide has the sequence: KPVSXSYRCPCRFFESHVARANVKHLKILN-TPNCALQIVARLKNNNRQVCIDPKLKWIQEYLEKAL-NK (SEQ ID NO:55) where X is any of the 20 proteinogenic amino acids except L, W or E. The most preferred of these peptides is SDF(L5P) which has the sequence: KPVSPSYR-CPCRFFESHVARANVKHLKILNTPNCALQIVARLKN-NNRQVCIDPKLKWIQEYLEKALNK (SEQ ID NO:56). Again, peptides that are truncated and which have at least the first eight amino acids of SEQ ID NO:55 or 56 are included in the invention. They may be extended at the C terminus by additional amino acids from the sequences shown above.

The longest mSDF-1 peptides presented above are 68 amino acids in length. However, unless otherwise indicated, it will also be understood that one additional proteinogenic amino acid may be added to the N terminus without substantially changing chemoattractant activity or MMP-2 resistance. Moreover, the addition of an amino acid at the N terminus represents a preferred embodiment since this will have the effect of making the peptide resistant to digestion by a second common peptidase, dipeptidyl peptidase IV (DP-PIV/CD26, abbreviated herein as "DPPIV").

DPPIV is a 110-kD glycoprotein which is expressed in renal proximal tubules, in intestinal epithelial cells, liver, placenta and lung and which cleaves peptides that have a proline in the second position from the N terminus (Kikawa, et al., *Biochim. Biophys. Acta* 1751:45-51 (2005)). SDF-1 has a proline in the second position (as can be seen above in SEQ ID NO:52) and is therefore cleaved by DPPIV between this proline and the following valine (Narducci, et al., *Blood* 107: 1108-1115 (2006); Christopherson, *Exp. Hematol.* 34:1060-1068 (2006)).

One way to eliminate the proteolytic effect of DPPIV would be to change the proline in position 2 of SDF-1 (see SEQ ID NO:52). However, this proline is essential for SDF-1's biological activity and therefore cannot be replaced and maintain a therapeutically effective peptide. However, activity can be maintained and a DPPIV resistant peptide made by adding one to four amino acids (or an organic group) to the N terminus of SEQ ID:52. For example, it has been experimentally found that resistance to DPPIV cleavage can be obtained by adding a serine to the N terminus of the peptide.

Thus, in another aspect, the invention is directed to the peptide $X_p$-SDF-1, where X is preferably, any proteinogenic amino acid, p is an integer between 1 and 4, and SDF-1 is as shown in SEQ ID NO:52. In preferred embodiments, n=1. It will be understood that when p is greater than 1, each of the 2-4 added amino acids may independently be chosen from any of the proteinogenic amino acids described herein, i.e., any of these proteinogenic amino acids may be in the first position, any in the second position, etc.

SDF-1 may also be made resistant to DPPIV by adding a "protease protective organic group" to the N-terminus. A "protease protective organic group" is defined herein as an organic group, other than a proteinogenic amino acid, that, when added to the N terminal amino acid of SDF-1, results in a modified peptide that maintains at least 10% (and preferably at least 50% or 80%) of the chemoattractant activity of unmodified SDF-1 (as determined by, e.g., assays of Jurkat T cell migration described herein) and which, in addition, is inactivated by DPPIV at a rate of less than 50% (and more preferably, at a rate of less than 25% or 10%) the rate of inactivation of unmodified SDF-1. For example, X may be: $R^1$—$(CH_2)_d$—, where d is an integer from 0-3, and $R^1$ is selected from: hydrogen (with the caveat that when $R^1$ is hydrogen, d must be at least 1); a branched or straight $C_1$-$C_3$ alkyl; a straight or branched $C_2$-$C_3$ alkenyl; a halogen, $CF_3$; —$CONR^5R^4$; —$COOR^5$; —$COR^5$; —$(CH_2)_qNR^5R^4$; —$(CH_2)_qSOR^5$; —$(CH_2)_qSOR^5$, —$(CH_2)_qSO_2NR^5R^4$; and $OR^5$, where $R^4$ and $R^5$ are each independently hydrogen or a straight or branched $C_1$-$C_3$ alkyl. In instances where an organic group is used for X, p should be 1. In addition, X may represent a proteinogenic amino acid as discussed above, so that 1-4 amino acids are added to SDF-1, and one or more of these added amino acids may be substituted with a protease protective organic group.

In the formula $X_p$-SDF-1, SDF-1 may optionally include any of the mutations in positions 4 and/or 5 of SEQ ID NO:52 as described above. Thus, the invention encompasses peptides of the form $X_p$-mSDF-1, where X and p are as defined above and mSDF-1 is selected from: SEQ ID NO:53; SEQ ID NO:54; SEQ ID NO:55; and SEQ ID NO:56. These doubly mutated peptides will be resistant to both DPPIV and MMP-2.

The invention also encompasses fusion proteins in which any of the above mSDF-1, $X_p$-SDF-1 or $X_p$-mSDF-1 sequences are linked to self-assembling peptides capable of forming a biologically compatible membrane. Membranes with attached protease resistant SDF-1 can be implanted in a patient at a site of tissue damage, especially cardiac tissue damage, wounds (whether accidental, surgical or the result of disease) or ulcers and will maintain the SDF-1 biological activity at that site for a prolonged period of time. Fusion proteins are formed either by joining the C terminal end of a protease resistant SDF-1 peptide directly to the N terminal end of a self-assembling peptide or the two peptides can be joined by a linker sequence. Thus, the invention includes fusion proteins of the formula: A-(L)$_n$-(R)$_q$, where n is an integer from 0-3, q is an integer from 1-3, A is one of the protease resistant SDF-1 peptides (i.e., mSDF-1, $X_p$-SDF-1 or $X_p$-mSDF-1) described above, L is a linker sequence 3-9 amino acids long, and R is a self-assembling peptide selected from the group consisting of:

```
AKAKAEAEAKAKAEAE,;       (SEQ ID NO: 1)

AKAEAKAEAKAEAKAE,;       (SEQ ID NO: 2)

EAKAEAKAEAKAEAKA,;       (SEQ ID NO: 3)

KAEAKAEAKAEAKAEA,;       (SEQ ID NO: 4)
```

-continued
```
AEAKAEAKAEAKAEAK,;       (SEQ ID NO: 5)

ADADARARADADARAR,;       (SEQ ID NO: 6)

ARADARADARADARAD,;       (SEQ ID NO: 7)

DARADARADARADARA,;       (SEQ ID NO: 8)

RADARADARADARADA,;       (SEQ ID NO: 9)

ADARADARADARADAR,;       (SEQ ID NO: 10)

ARADAKAEARADAKAE,;       (SEQ ID NO: 11)

AKAEARADAKAEARAD,;       (SEQ ID NO: 12)

ARAKADAEARAKADAE,;       (SEQ ID NO: 13)

AKARAEADAKARADAE,;       (SEQ ID NO: 14)

AQAQAQAQAQAQAQAQ,;       (SEQ ID NO: 15)

VQVQVQVQVQVQVQVQ,;       (SEQ ID NO: 16)

YQYQYQYQYQYQYQYQ,;       (SEQ ID NO: 17)

HQHQHQHQHQHQHQHQ,;       (SEQ ID NO: 18)

ANANANANANANANAN,;       (SEQ ID NO: 19)

VNVNVNVNVNVNVNVN,;       (SEQ ID NO: 20)

YNYNYNYNYNYNYNYN,;       (SEQ ID NO: 21)

HNHNHNHNHNHNHNHN,;       (SEQ ID NO: 22)

ANAQANAQANAQANAQ,;       (SEQ ID NO: 23)

AQANAQANAQANAQAN,;       (SEQ ID NO: 24)

VNVQVNVQVNVQVNVQ,;       (SEQ ID NO: 25)

VQVNVQVNVQVNVQVN,;       (SEQ ID NO: 26)

YNYQYNYQYNYQYNYQ,;       (SEQ ID NO: 27)

YQYNYQYNYQYNYQYN,;       (SEQ ID NO: 28)

HNHQHNHQHNHQHNHQ,;       (SEQ ID NO: 29)

HQHNHQHNHQHNHQHN,;       (SEQ ID NO: 30)

AKAQADAKAQADAKAQAD,;     (SEQ ID NO: 31)

VKVQVDVKVQVDVKVQVD,;     (SEQ ID NO: 32)

YKYQYDYKYQYDYKYQYD,;     (SEQ ID NO: 33)

HKHQHDHKHQHDHKHQHD,;     (SEQ ID NO: 34)

RARADADARARADADA,;       (SEQ ID NO: 35)

RADARGDARADARGDA,;       (SEQ ID NO: 36)

RAEARAEARAEARAEA,;       (SEQ ID NO: 37)

KADAKADAKADAKADA,;       (SEQ ID NO: 38)

AEAEAHAHAEAEAHAH,;       (SEQ ID NO: 39)

FEFEFKFKFEFEFKFK,;       (SEQ ID NO: 40)

LELELKLKLELELKLK,;       (SEQ ID NO: 41)

AEAEAKAKAEAEAKAK,;       (SEQ ID NO: 42)

AEAEAEAEAKAK,;           (SEQ ID NO: 43)

KAKAKAKAEAEAEAEA,;       (SEQ ID NO: 44)

AEAEAEAEAKAKAKAK,;       (SEQ ID NO: 45)
```

```
RARARARADADADADA,;         (SEQ ID NO: 46)

ADADADADARARARAR,;         (SEQ ID NO: 47)

DADADADARARARARA,;         (SEQ ID NO: 48)

HEHEHKHKHEHEHKHK,;         (SEQ ID NO: 49)

VEVEVEVEVEVEVEVE,;         (SEQ ID NO: 50)
and

RFRFRFRFRFRFRFRFRF,.       (SEQ ID NO: 51)
``` tease resistant peptides or fusion proteins described above, vectors in which these nucleic acids are operably linked to a promoter sequence and host cells transformed with the vectors. The term "operably linked" refers to genetic elements that are joined in a manner that enables them to carry out their normal functions. For example, a sequence encoding a peptide is operably linked to a promoter when its transcription is under the control of the promoter and the transcript produced is correctly translated into the peptide.

Preferred nucleic acids encoding protease resistant SDF-1 peptides and fusion proteins include:

```
                                                                  (SEQ ID NO: 60)
aagcccgtcgtcctgagctacagatgcccatgccgattcttcgaaagccatgttgccagagccaacgtcaagc atctcaaaattctcaacactccaaactgtgcccttcagattgtagcccggctgaagaacaacaacagacaagtgt gcattgacccgaagctaaagtggattcaggagtacctggagaaagctttaaacaag;

(SEQ ID NO: 61)
aagcccgtcgtcctgagctacagatgcccatgccgattcttcgaaagccatgttgccagagccaacgtcaagc atctcaaaattctcaacactccaaactgtgcccttcagattgtagcccggctgaagaacaacaacagacaagtgt gcattgacccgaagctaaagtggattcaggagtacctggagaaagctttaaacaagtgaggaatcgtgggacc tctgcgtgcccgtgccgacgccgacgcccgtgcccgtgccgacgccgacgcc;

(SEQ ID NO: 62)
aagcccgtcgtcctgagctacagatgcccatgccgattcttcgaaagccatgttgccagagccaacgtcaagc atctcaaaattctcaacactccaaactgtgcccttcagattgtagcccggctgaagaacaacaacagacaagtgt gcattgacccgaagctaaagtggattcaggagtacctggagaaagctttaaacaagcctgtgggactgatcgg agtgcccgtgccgacgccgacgcccgtgcccgtgccgacgccgacgcc;
and (SEQ ID NO: 63)
aagcccgtcgtcctgagctacagatgcccatgccgattcttcgaaagccatgttgccagagccaacgtcaagc atctcaaaattctcaacactccaaactgtgcccttcagattgtagcccggctgaagaacaacaacagacaagtgt gcattgacccgaagctaaagtggattcaggagtacctggagaaagctttaaacaagggaggcgggggaggt gggcgtgcccgtgccgacgccgacgcccgtgcccgtgccgacgccgacgcc
```

The most preferred self-assembling peptide is: RARADADARARADADA, (SEQ ID NO:35) with q=1; and preferred protease resistant SDF-1 peptides are SDF(S4V) and $X_p$-SDF (S4V), especially where p=1. When joined together, the resulting fusion proteins are, for convenience, abbreviated as SDF(S4V)-RAD or $X_p$-SDF(S4V)-RAD. Preferred linker sequences occur when n=1 and L is GGGGGG (abbreviated as "6G," SEQ ID NO:57); GIVGPL (SEQ ID NO:58) and PVGLIG (SEQ ID NO:59). The lattermost represents an MMP-2 cleavage site ("MCS"). GIVGPL (SEQ ID NO:58) represents a scrambled version of MCS and is abbreviated as "SCR." Surprisingly, this sequence was also found to undergo MMP-2 cleavage, although at a slower rate than MCS. Preferred, fusion proteins containing linker sequences are: SDF(S4V)-6G-RAD; $X_p$-SDF(S4V)-6G-RAD; SDF(S4V)-MCS-RAD; $X_p$-SDF(S4V)-MCS-RAD; SDF(S4V)-SCR-RAD; and XP-SDF(S4V)-SCR-RAD. Again, p is preferably 1.

In another aspect, the invention is directed to nucleic acids comprising a nucleotide sequence encoding any of the protease resistant peptides or fusion proteins described above, In another aspect, the invention is directed to a biologically compatible membrane formed from self-assembling peptides as described in published US applications 20060148703 and 20060088510 which have mSDF-1, Xp-SDF-1 or Xp-mSDF-1 peptides attached. The term "biologically compatible" indicates that the membranes are non-toxic and can be implanted in a patient without triggering an immune response. Between 0.1% and 10% (and preferably 0.5-5%) of the peptides that assemble into the membrane are bound to a mutant SDF-1. Binding may be either covalent or noncovalent. Noncovalent bonding occurs when protease resistant SDF-1 peptides are simply trapped in the membrane matrix and when protease resistant SDF-1 peptides are bound to self-assembling peptides in the membrane by biotin/avidin linkages. As used herein, the term "avidin" is intended to include streptavidin as well. The membranes may, optionally, have other therapeutic agents, e.g., PDGF or interleukin-8, attached as well.

The use of biotin and avidin for linking molecules is well known in the art and standard methodology can be used for attaching protease resistant SDF-1 peptides to self-assembling peptides either before or after membrane formation.

Specific methodology for using biotin/avidin in connection with self-assembling membranes has been described in US 20060088510 and this methodology can be applied to forming membranes with attached cytokine. In order to prevent steric interference between the biotin/avidin groups and protease resistant peptides, a spacer may be included between the two. The spacer can take the form of 1-15 (preferably 1-10) fatty acids or 1-15 (preferably)-10) amino acids and should separate the protease resistant SDF-1 peptide from the self-assembling peptide by at least an additional 12 angstroms and by no more than an additional 250 angstroms. Methodology for incorporating spacers of this type is well known in the art. In a preferred embodiment, about 1% of the self-assembling peptides used in membranes are attached to protease resistant SDF-1. It is also preferable that the self-assembling peptides making up membranes be homogeneous, i.e., that all of the peptides are identical.

As an alternative, protease resistant SDF-1 peptides may be joined to a self-assembling peptide that is part of the membrane by a peptide bond, i.e., the protease resistant SDF-1 may be part of a fusion protein in which it is joined to a self-assembling peptide either directly or via an intervening linker amino acid sequence. Any of the fusion proteins described above may be used, with SDF(S4V)-6G-RAD; $X_p$-SDF(S4V)-6G-RAD; SDF(S4V)-MCS-RAD; $X_p$-SDF(S4V)-MCS-RAD; SDF(S4V)-SCR-RAD and $X_p$-SDF(S4V)-SCR-RAD being particularly preferred. The membranes are made from the fusion proteins (or from the self-assembling peptides) by taking advantage of the fact that the self-assembling peptides described herein do not congregate together in water, but assemble into a membrane in the presence of a low concentration of monovalent metal cation. Thus, for example, fusion proteins may be made under conditions in which self-assembly does not occur and then exposed to conditions that promote membrane formation, e.g., low monovalent metal cation concentration. The end result is a matrix which can be implanted into a patient and which will maintain a high concentration of SDF-1 biological activity at the site of implantation. Alternatively, the fusion proteins can be incorporated into an injectable pharmaceutical composition at a concentration of monovalent cation that is too low to induce self-assembly and can then administered to a patient to induce membrane formation in vivo.

The mutated SDF-1 peptides are resistant to cleavage by MMP-2 and/or DPPIV but maintain at least a portion (at least 10% and preferably more than 25%, 50% or 80%) of the chemoattractant activity of native SDF-1. Thus, they are ideally suited for use at sites, such as damaged cardiac tissue, where MMP-2 (or DPPIV) is present at a high concentration. In addition, an MMP-2 cleavage site can, if desired, be placed in linker regions joining the SDF-1 peptides to the self-assembling peptides. This will allow for the protease resistant SDF-1 peptides to be released from an implanted membrane over time.

The compositions described above should be useful in the treatment of any disease or condition characterized by high concentrations of MMP-2 and/or DPPIV where attraction of stem cells might induce regeneration or healing. This would include the treatment of inflammatory and ischemic diseases such as stroke, limb ischemia; wound healing: and diabetic ulcers. In an especially preferred embodiment, the invention is directed to a method of treating damaged cardiac tissue, for example subsequent to a heart attack, by injecting or implanting any of the biologically compatible peptide membranes or fusion proteins described above at or near the site of damage. Preferably, membranes will be injected or implanted directly into the damaged tissue, e.g., myocardium, of a patient. The membranes should be large enough to prevent the protease resistant SDF-1 from being washed away by bodily fluids and a sufficient amount of mSDF-1 should be present to promote the migration of T cells to the site of injury. Guidance with regard to these parameters is provided by the experiments described herein.

DESCRIPTION OF THE INVENTION

The present invention is based upon the concept that the recovery of damaged tissue, e.g., damaged cardiac tissue, is promoted by exposing the tissue to SDF-1 that has been mutated to make it resistant to MMP-2 and/or DPPIV cleavage and which is delivered by means of a membrane formed by spontaneously assembling peptides. The self-assembling peptides have been described in U.S. Pat. Nos. 5,670,483 and 6,548,630 (hereby incorporated by reference in their entirety). Methods of attaching factors to membranes and the use of the membranes in delivering therapeutic agents to cardiac tissue have also been described (see published US applications 20060148703 and 20060088510, hereby incorporated by reference in their entirety). The same procedures for making and using membranes may be applied to the present invention.

Description of Self-Assembling Peptides

The peptides used for self-assembly should be at least 12 residues in length and contain alternating hydrophobic and hydrophilic amino acids. Peptides longer than about 200 amino acids tend to present problems with respect to solubility and membrane stability and should therefore be avoided. Ideally, peptides should be about 12-24 amino acids in length.

The self-assembling peptides must be complementary. This means that the amino acids on one peptide must be capable of forming ionic bonds or hydrogen bonds with the amino acids on another peptide. Ionic bonds would form between acidic and basic amino acid side chains. The hydrophilic basic amino acids include Lys, Arg, His, and Orn. The hydrophilic acidic amino acids are Glu and Asp. Ionic bonds would form between an acidic residue on one peptide and a basic residue on another. Amino acids that form hydrogen bonds are Asn and Gln. Hydrophobic amino acids that may be incorporated into peptides include Ala, Val, Ile, Met, Phe, Tyr, Trp, Ser, Thr, and Gly.

Self-assembling peptides must also be "structurally compatible." This means that they must maintain an essentially constant distance between one another when they bind. Interpeptide distance can be calculated for each ionized or hydrogen bonding pair by taking the sum of the number of unbranched atoms on the side-chains of each amino acid in the pair. For example, lysine has five and glutamic acid has four unbranched atoms on their side chains. An interaction between these two residues on different peptides would result in an interpeptide distance of nine atoms. In a peptide containing only repeating units of EAK, all of the ion pairs would involve lysine and glutamate and therefore a constant interpeptide distance would be maintained. Thus, these peptides would be structurally complementary. Peptides in which the variation in interpeptide distance varies by more than one atom (about 3-4 angstroms) will not form gels properly. For example, if two bound peptides have ion pairs with a nine-atom spacing and other ion pairs with a seven-atom spacing, the requirement of structural complementarity would not have been met. A full discussion of complementarity and structural compatibility may be found in U.S. Pat. Nos. 5,670,483 and 6,548,630.

It should also be recognized that membranes may be formed from either a homogeneous mixture of peptides or a heterogeneous mixture of peptides. The term "homogeneous" in this context means peptides that are identical with one another. "Heterogeneous" indicates peptides that bind to one another but which are structurally different. Regardless of whether homogenous or heterogeneous peptides are used, the requirements with respect to the arrangement of amino acids, length, complementarity, and structural compatibility apply. In addition, it should be recognized that the carboxyl and amino groups of the terminal residues of peptides can either be protected or not protected using standard groups.

Making of Peptides

The self-assembling and protease resistant SDF-1 peptides of the present invention can be made by solid-phase peptide synthesis using standard N-tert-butyoxycarbonyl (t-Boc) chemistry and cycles using n-methylpyrolidone chemistry. Once peptides have been synthesized, they can be purified using procedures such as high pressure liquid chromatography on reverse-phase columns. Purity may also be assessed by HPLC and the presence of a correct composition can be determined by amino acid analysis. A purification procedure suitable for mSDF-1 peptides is described in the Examples section.

Fusion proteins may either be chemically synthesized or made using recombinant DNA techniques. The full sequences of these proteins are described herein and examples are provided of DNA sequences that can be used in producing them.

Binding of SDF-1 to Self-Assembling Peptides

Several strategies may be used for attaching protease resistant SDF-1 to self-assembling peptides. One strategy is non-covalent binding which has previously been shown to be effective in delivering PDGF-BB, a growth factor, to tissues (Hsieh, et al., *J. Clin. Invest.* 116:237-248 (2006)).

A second attachment strategy is the biotin-sandwich method (Davis, et al., *Proc. Nat'l Acad. Sci. USA* 103:8155-8160 (2006)) in which a protease resistant SDF-1 is biotinylated and bound to biotinylated peptides using tetravalent streptavidin as a linker. To accomplish this, the protease resistant SDF-1 may be coupled to the 15 amino acid sequence of an acceptor peptide for biotinylation (referred as AP; Chen, et al., *Nat. Methods* 2:99-104 (2005)). Because the active site of SDF-1 is situated near the amino terminus, fusion proteins should be made by incorporating the extra sequences at the C-terminus. The acceptor peptide sequence allows site-specific biotinylation by the *E. coli* enzyme biotin ligase (BirA; Chen, et al., *Nat. Methods* 2:99-104 (2005)). Many commercial kits are available for biotinylating proteins. However, many of these kits biotinylate lysine residues in a nonspecific manner, and this may reduce mSDF-1 activity as it has been shown that the N-terminal lysine of SDF-1 is crucial for receptor binding and activity (Crump, et al, *EMBO J.* 16:6996-7007 (1997)). Biotinylated self-assembling peptides are made by MIT Biopolymers laboratory and when mixed in a 1 to 100 ratio with native self-assembling peptides, self-assembly of nanofibers should not be disturbed (Davis, et al., *Proc. Nat'l Acad. Sci. USA* 103:8155-8160 (2006)).

A third targeting strategy is direct incorporation of protease resistant SDF-1 peptides into self-assembling nanofibers by construction of a fusion protein of mutated SDF-1 with a self-assembling peptide. For example an mSDF-1 may be coupled to the 16 amino acid sequence of SEQ ID NO:35. This "RAD" portion of the fusion protein will incorporate into the nanofiber scaffold while assembling.

Formation of Membranes

The self-assembling peptides and fusion proteins described herein will not form membranes in water, but will assemble in the presence of a low concentration of monovalent metal cation. The order of effectiveness of these cations is $Li^+>Na^+>K^+>Cs^+$ (U.S. Pat. No. 6,548,630). A concentration of monovalent cation of 5 mM should be sufficient for peptides to assemble and concentrations as high as 5 M should still be effective. The anion associated with the monovalent cation is not critical to the invention and can be acetate, chloride, sulfate, phosphate, etc.

The initial concentration of self-assembling peptide will influence the final size and thickness of membranes formed. In general, the higher the peptide concentration, the higher the extent of membrane formation. Formation can take place at peptide concentrations as low as 0.5 mM or 1 mg/ml. However, membranes are preferably formed at higher initial peptide concentrations, e.g., 10 mg/ml, to promote better handling characteristics. Overall, it is generally better to form membranes by adding peptides to a salt solution rather than adding salt to a peptide solution.

The formation of membranes is relatively unaffected by pH or by temperature. Nevertheless, pH should be maintained below 12 and temperatures should generally be in the range of 4-90° C. Divalent metal cations at concentrations equal to or above 100 mM result in improper membrane formation and should be avoided. Similarly, a concentration of sodium dodecyl sulfate of 0.1% or higher should be avoided.

Membrane formation may be observed by simple visual inspection and this can be aided, if desired, with stains such as Congo Red. The integrity of membranes can also be observed microscopically, with or without stain.

Pharmaceutical Compositions and Dosages

Membranes with attached protease resistant SDF-1 peptides or fusion proteins may be incorporated into a pharmaceutical composition containing a carrier such as saline, water, Ringer's solution and other agents or excipients. The dosage form will generally be designed for implantation or injection, particularly into cardiac tissue but topical treatments will also be useful, e.g., in the treatment of wounds. All dosage forms may be prepared using methods that are standard in the art (see e.g., *Remington's Pharmaceutical Sciences*, 16th ed. A. Oslo. ed., Easton, Pa. (1980)).

It is expected that the skilled practitioner will adjust dosages on a case by case basis using methods well established in clinical medicine. The optimal dosage will be determined by methods known in the art and will be influenced by factors such as the age of the patient, disease state and other clinically relevant factors.

EXAMPLES

Example 1

Biological Effects and Protease Resistance of SDF-1 Mutants

SDF-1 Purification and Expression

The DNA sequence of mature SDF-1α may be cloned from human cDNA into pET-Sumo vector and an extra N-terminal serine residue may be incorporated to facilitate cleavage by Sumo protease (yielding an SDF-1 form of 69 AA). Fusion proteins may be made by incorporating RAD or AP sequences in reverse primers. Sumo-SDF-1 fusion proteins are expressed in Rosetta DE3 *E coli* and grown to an optical density of 1.5 (600 nm) at 37° C. Cells are induced with 0.25 mM isopropyl β-D-thiogalactoside for 4 h and harvested by centrifugation. As described below, SDF-1α may be purified by a 3-step procedure; all steps being performed at 21° C.

Cells from a 4-L growth were lysed in 300 ml lysis buffer (6M Guanidine, 20 mM phosphate (pH 7.8), 500 mM NaCl) and homogenized. Debris is collected by centrifugation at 3000 g. The first purification step consisted of capture of the poly-histidine tag present in the SUMO-SDF-1α fusion protein with Nickel-NTA. Nickel-NTA resin was washed with wash buffer (8M Urea, 500 mM NaCl, 20 mM phosphate (pH 6.2)) and the bound protein was eluted at pH 4. Further purification and oxidative refolding were performed on a Cation Exchange HPLC column. The sample was adjusted to binding buffer (8M Urea, 30 mM 2-mercaptoethanol, 1 mM EDTA, 50 mM Tris pH8) and loaded on the HPLC column. Refolding of Sumo-SDF-1 was performed on the column with a 2 h run of refolding buffer (50 mM Tris pH8, 75 mM NaCl, 0.1 mM reduced Glutathione and 0.1 mM oxidized Glutathione). Sumo-SDF-1 was eluted with a step gradient (0.5 to 1M NaCl) and concentrated. The SUMO-SDF-1 fusion protein was cleaved by Sumo Protease 1 (1 U/50 µg protein) in 50 mM Tris pH 8.0, 500 mM NaCl. The sample was adjusted to 0.1% trifluoroacetic acid (TFA) and loaded on a C18 Reversed Phase HPLC column for the final purification step. The column was subjected to a linear gradient from 30 to 40% acetonitrile in 0.1% TFA. The fractions containing SDF-1 were lyophilized and resuspended. Activity of purified SDF-1 was tested by migration of Jurkat T-lymphocyte cell line.

Modification of SDF-1 Constructs

SDF-1 fusion constructs were modified by insertional mutagenesis with one of three sequences: one sequence is susceptible to MMP-2 cleavage (MMP cleavage site or MCS), another sequence contains the same amino acids but in a random order (scrambled sequence, or SCR), and the third sequence contains 6 glycines as a linker.

Mutations of the MMP Cleavage Sites in Chemokines

SDF-1 is cleaved by MMP-2 in its active site at the N-terminus, leaving an N-terminal tetrapeptide and inactive SDF-1(5-68). Specific mutagenesis of 4 different amino acids was performed in order to render SDF-1 resistant to MMP-2 cleavage, based on substrate sequences of MMP-2 described by Netzel-Arnett et al (*Biochemistry* 32:6427-6432 (1993)). The four different constructs were expressed and purified as described for SDF-1. Of the 4 different mutations, SDF-1 (L5W) and SDF-1(L5E) showed minimal activity on T-cell migration. In contrast, SDF-1(S4V) and SDF-1(L5P) showed bioactivity comparable to native SDF-1. Because SDF-1 (L5P) was more difficult to purify, SDF-1(S4V) was selected for further experiments.

Effect of Mutations on Protease Susceptibility and Chemoattractant Activity

The mutated forms of SDF-1 were examined in an assay of migration of Jurkat T cells at a concentration of 100 nM. This assay indicated that both SDF-1(S4V) and SDF-1(L5P) retained most of the activity of unmutated SDF-1 in promoting T cell migration. This activity was greatly reduced in SDF-1(L5W) mutants and SDF-1(L5E) mutants.

The susceptibility of the peptides to cleavage by MMP-2 was determined by incubating the mutants with the enzyme for one hour and then examining the incubation product by SDS-PAGE. This revealed that, unlike SDF-1, the mutants did not undergo a positional shift indicative of cleavage. MMP-2 incubation was also found to reduce the chemoattractant activity of SDF-1 but not SDF-1(S4V) as shown by a Jurkat T-cell migration assay. These results suggest that the S4V variant of SDF-1 retains chemokine bioactivity but is resistant to activation by MMP-2.

In Vivo Data

A blinded and randomized study was performed to evaluate the effect of different SDF-1 forms on cardiac function after myocardial infarction in rats. Ejection fraction was measured with a Millar catheter system for measurement of intraventricular pressures and ventricular volumes. Both SDF-1 (S4V)-6G-RAD and SDF-1(S4V)-MCS-RAD significantly increased cardiac function 4 weeks after myocardial infarction in rats compared to MI only group. This indicates that both MMP-2 resistance (SDF-1(S4V)) and attachment to membranes are necessary for successful cardiac repair therapy.

Example 2

Experiments with Truncated Forms of SDF-1

3 truncated forms of SDF-1 were synthesized commercially; all include the first 17 amino acids of native SDF-1. Two variants of SDF-1 17AA were designed to be more resistant to MMP-2, based on our prior work with the entire SDF-1 protein:

```
SDF-1 17AA:
KPVSLSYRCPCRFFESH          (SEQ ID 64)

SDF-1(S4V) 17AA:
KPVVLSYRCPCRFFESH          (SEQ ID 65)

SDF-1(L5P) 17AA:
KPVSPSYRCPCRFFESH          (SEQ ID 66)
```

Migration experiments were performed with the Jurkat T-lymphocyte cell line. Truncated SDF-1 17AA was 500 times less potent than native SDF-1 but maximal migration induced was similar to native SDF-1. Therefore, if 500 times higher concentrations were used compared to full-length protein, the same migratory response of T-lymphocytes should be observed. The mutated SDF-1(S4V) 17AA and SDF-1 (L5P) 17AA were three times less potent than SDF-1 17AA without mutation. This is a similar shift to that seen between native SDF-1 and SDF-1(S4V).

Cleavage experiments of the peptides with MMP-2 were performed: 2 nmole of SDF-1 17AA, SDF-1(S4V) 17AA, and SDF-1(L5P) 17AA were incubated with MMP-2 for 1 h at RT. Proteins were run on an SDS-PAGE showing cleavage of SDF-1 17AA, but not of SDF-1(S4V) 17AA or SDF-1 (L5P) 17AA. Thus, these truncated proteins may be useful therapeutically, as they are still bioactive and also MMP-2 resistant.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. An isolated mutant form of stromal cell derived factor-1 (SDF-1) peptide comprising the formula of $X_p$-mSDF-1, wherein said mSDF-1 in said $X_p$-mSDF-1 comprises the amino acid sequence of at least amino acids 1-8 of SDF-1 amino acid sequence consisting of SEQ ID NO:52 and which is optionally extended at the C terminus of amino acids 1-8 of SEQ ID NO: 52 by all or any portion of the remaining sequence of SEQ ID NO:52, shown as amino acids 9-68 of the full-length of SEQ ID NO: 52 and said amino acids 1-8 comprises a mutation at the fourth or the fourth and the fifth amino acids from the N terminus of said amino acids 1-8 of SEQ ID NO:52, and wherein:
   a) X is serine;
   b) p equals one; and
   c) said mutant form comprising $X_p$-mSDF-1 has chemoattractant activity for T cells, is inactivated by dipeptidyl peptidase IV (DPPIV) at a rate that is less than one-half of the rate at which native SDF-1 is inactivated, and is inactivated by MMP-2 at a rate that is less than one-half of the rate at which native SDF-1 is inactivated.

2. The isolated mutant form of SDF-1 peptide of claim 1, wherein said $X_p$-mSDF-1 peptide has a mutation of serine to valine at the fourth amino acid from the N terminus of said amino acids 1-8 of SEQ ID NO:52.

3. The isolated mutant form of SDF-1 peptide of claim 1, wherein said $X_p$-mSDF-1 peptide has a mutation of serine to valine at the fourth amino acid and leucine to proline at the fifth amino acid from the N terminus of said amino acids 1-8 of SEQ ID NO:52.

4. The isolated mutant form of SDF-1 peptide of claim 1, wherein said mutation of the fifth amino acid from the N terminus of amino acids 1-8 of SEQ ID NO:52 is not a mutation to a tryptophan or a glutamic acid amino acid residue.

5. An isolated mutant form of stromal cell derived factor-1 (SDF-1) peptide comprising the formula of $X_p$-mSDF-1, wherein said mSDF-1 in said $X_p$-mSDF-1 comprises the amino acid sequence of at least amino acids 1-17 of SDF-1 amino acid sequence consisting of SEQ ID NO:52 and which is optionally extended at the C-terminus of amino acids 1-17 of SEQ ID NO: 52 by all or any portion of the remaining sequence of SEQ ID NO:52, shown as amino acids 18-68, and wherein said amino acids 1-17 comprise a mutation at the fourth or the fifth, or mutations at the fourth and the fifth amino acids from the N terminus of said amino acids 1-17 of SEQ ID NO:52, and wherein:
   a) X is serine;
   b) p equals one; and
   c) said mutant form comprising $X_p$-mSDF-1 has chemoattractant activity for T cells, is inactivated by DPPIV at a rate that is less than one-half of the rate at which native SDF-1 is inactivated, and is inactivated by MMP-2 at a rate that is less than one-half of the rate at which native SDF-1 is inactivated.

6. The isolated mutant form of SDF-1 peptide of claim 5, wherein said $X_p$-mSDF-1 peptide has a mutation of serine to valine at the fourth amino acid from the N terminus of said amino acids 1-17 of SEQ ID NO:52.

7. The isolated mutant form of SDF-1 peptide of claim 5, wherein said $X_p$-mSDF-1 peptide has a mutation of leucine to proline at the fifth amino acid from the N terminus of said amino acids 1-17 of SEQ ID NO:52.

8. The isolated mutant form of SDF-1 peptide of claim 5, wherein said mutation of the fifth amino acid from the N terminus of amino acids 1-17 of SEQ ID NO:52 is not a mutation to a tryptophan or a glutamic acid amino acid residue.

9. An isolated mutant form of SDF-1 peptide comprising the formula of $X_p$-mSDF-1, wherein said mSDF-1 in said X-mSDF-1 comprises the amino acid sequence of at least amino acids 1-8 of SDF-1 amino acid sequence consisting of SEQ ID NO:52 and which is optionally extended at the C-terminus of amino acids 1-8 of SEQ ID NO: 52 by all or any portion of the remaining sequence of SEQ ID NO:52, shown as amino acids 9-68 of the full-length of SEQ ID NO:52, and wherein said amino acids 1-8 of SEQ ID NO:52 comprise a mutation at the fourth or the fifth, or mutations at the fourth and the fifth amino acids from the N-terminus of said amino acids 1-8 of SEQ ID NO:52, and wherein:
   a) X is serine;
   b) p equals one; and
   c) said mutant form comprising $X_p$-mSDF-1 has chemoattractant activity for T cells, is inactivated by DPPIV at a rate that is less than one-half of the rate at which native SDF-1 is inactivated, and is inactivated by MMP-2 at a rate that is less than one-half of the rate at which native SDF-1 is inactivated.

10. The isolated mutant form of SDF-1 peptide of claim 9, wherein said $X_p$-mSDF-1 peptide has a mutation of serine to valine at the fourth amino acid from the N terminus of said amino acids 1-8 of SEQ ID NO:52.

11. The isolated mutant form of SDF-1 peptide of claim 9, wherein said $X_p$-mSDF-1 peptide has a mutation of leucine to proline at the fifth amino acid from the N terminus of said amino acids 1-8 of SEQ ID NO:52.

12. The isolated mutant form of SDF-1 peptide of claim 9, wherein said mutation of the fifth amino acid from the N-terminus of said amino acids 1-8 of SEQ ID NO:52 peptide is not a mutation to a tryptophan or a glutamic acid amino acid residue.

13. The isolated mutant form of SDF-1 peptide of claim 1, 5, or 9, wherein said $X_p$-mSDF-1 peptide mutant form maintains chemoattractant activity for T cells of at least 10% that of native SDF-1 and is inactivated by MMP-2 at a rate that is less than one-fourth of the rate of inactivation of native SDF-1.

14. An isolated mutant form of stromal cell derived factor-1 (SDF-1) peptide comprising the formula of mSDF-1 or $X_p$-mSDF-1, wherein said mSDF-1 or said mSDF-1 in said $X_p$-mSDF-1 comprises the amino acid sequence of at least amino acids 1-8 of SDF-1 amino acid sequence consisting of SEQ ID NO:52 wherein said amino acids 1-8 of SEQ ID NO:52 comprise mutations of serine to valine at the fourth amino acid and leucine to proline at the fifth amino acid from the N terminus of said amino acids 1-8 of SEQ ID NO:52, and which is optionally extended at the C-terminus of amino acids 1-8 of SEQ ID NO: 52 by all or any portion of the remaining sequence of SEQ ID NO:52, shown as amino acids 9-68 of the full-length of SEQ ID NO: 52, and wherein:
  a) X is a proteinogenic amino acid or a protease protective organic group;
  b) p is any integer from 1 to 4;
  c) said mutant form comprising mSDF-1 has chemoattractant activity for T cells and is inactivated by matrix metalloproteinase-2 (MMP-2) at a rate that is less than one-half of the rate at which native SDF-1 peptide is inactivated; and
  d) said mutant form comprising $X_p$-mSDF-1 has chemoattractant activity for T cells, is inactivated by dipeptidyl peptidase IV (DPPIV) at a rate that is less than one-half of the rate at which native SDF-1 is inactivated, and is inactivated by MMP-2 at a rate that is less than one-half of the rate at which native SDF-1 is inactivated.

15. The isolated mutant form of claim 14 comprising said mSDF-1 or said $X_p$-mSDF-1 maintains chemoattractant activity for T cells of at least 10% that of native SDF-1 and is inactivated by MMP-2 at a rate that is less than one-fourth of the rate of inactivation of native SDF-1.

* * * * *

UNITED STATES PATENT AND TRADEMARK OFFICE
CERTIFICATE OF CORRECTION

| | | |
|---|---|---|
| PATENT NO. | : 7,999,067 B2 | Page 1 of 1 |
| APPLICATION NO. | : 12/683253 | |
| DATED | : August 16, 2011 | |
| INVENTOR(S) | : Richard T. Lee and Vincent Segers | |

It is certified that error appears in the above-identified patent and that said Letters Patent is hereby corrected as shown below:

In Column 42, lines 7-8 (Claim 15), as described here:

replace

"15. The isolated mutant form of claim 14 comprising said mSDF-1 or said $X_p$-mSDF-1 maintains chemoattractant activity for T cells of at least 10% that of native SDF-1 and is inactivated by MMP-2 at a rate that is less than one-fourth of the rate of inactivation of native SDF-1."

with

--15. The isolated mutant form of claim 14 comprising said mSDF-1 or said $X_p$-mSDF-1 wherein said mutant form maintains chemoattractant activity for T cells of at least 10% that of native SDF-1 and is inactivated by MMP-2 at a rate that is less than one-fourth of the rate of inactivation of native SDF-1.--

Signed and Sealed this
Eighth Day of November, 2011

David J. Kappos
*Director of the United States Patent and Trademark Office*

SEQUENCE LISTING

<160> NUMBER OF SEQ ID NOS: 66

<210> SEQ ID NO 1
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 1

Ala Lys Ala Lys Ala Glu Ala Glu Ala Lys Ala Lys Ala Glu Ala Glu
1               5                   10                  15

<210> SEQ ID NO 2
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 2

Ala Lys Ala Glu Ala Lys Ala Glu Ala Lys Ala Glu Ala Lys Ala Glu
1               5                   10                  15

<210> SEQ ID NO 3
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 3

Glu Ala Lys Ala Glu Ala Lys Ala Glu Ala Lys Ala Glu Ala Lys Ala
1               5                   10                  15

<210> SEQ ID NO 4
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 4

Lys Ala Glu Ala Lys Ala Glu Ala Lys Ala Glu Ala Lys Ala Glu Ala
1               5                   10                  15

<210> SEQ ID NO 5
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 5

Ala Glu Ala Lys Ala Glu Ala Lys Ala Glu Ala Lys Ala Glu Ala Lys
1               5                   10                  15

<210> SEQ ID NO 6
<211> LENGTH: 16
<212> TYPE: PRT
<213> ORGANISM: Artificial
<220> FEATURE:
<223> OTHER INFORMATION: synthetic sequence designed for self assembly

```
<400> SEQUENCE: 6

Ala Asp Ala Asp Ala Arg Ala Arg Ala Asp Ala Asp Ala Arg Ala Arg
1               5                   10                  15

<210> SEQ ID NO 7
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 7

Ala Arg Ala Asp Ala Arg Ala Asp Ala Arg Ala Asp Ala Arg Ala Asp
1               5                   10                  15

<210> SEQ ID NO 8
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 8

Asp Ala Arg Ala Asp Ala Arg Ala Asp Ala Arg Ala Asp Ala Arg Ala
1               5                   10                  15

<210> SEQ ID NO 9
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 9

Arg Ala Asp Ala Arg Ala Asp Ala Arg Ala Asp Ala Arg Ala Asp Ala
1               5                   10                  15

<210> SEQ ID NO 10
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 10

Ala Asp Ala Arg Ala Asp Ala Arg Ala Asp Ala Arg Ala Asp Ala Arg
1               5                   10                  15

<210> SEQ ID NO 11
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 11

Ala Arg Ala Asp Ala Lys Ala Glu Ala Arg Ala Asp Ala Lys Ala Glu
1               5                   10                  15

<210> SEQ ID NO 12
<211> LENGTH: 16
<212> TYPE: PRT
<213> ORGANISM: Artificial
<220> FEATURE:
<223> OTHER INFORMATION: synthetic sequence designed for self assembly
```

```
<400> SEQUENCE: 12

Ala Lys Ala Glu Ala Arg Ala Asp Ala Lys Ala Glu Ala Arg Ala Asp
1               5                   10                  15

<210> SEQ ID NO 13
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 13

Ala Arg Ala Lys Ala Asp Ala Glu Ala Arg Ala Lys Ala Asp Ala Glu
1               5                   10                  15

<210> SEQ ID NO 14
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 14

Ala Lys Ala Arg Ala Glu Ala Asp Ala Lys Ala Arg Ala Asp Ala Glu
1               5                   10                  15

<210> SEQ ID NO 15
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 15

Ala Gln Ala Gln Ala Gln Ala Gln Ala Gln Ala Gln Ala Gln Ala Gln
1               5                   10                  15

<210> SEQ ID NO 16
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 16

Val Gln Val Gln Val Gln Val Gln Val Gln Val Gln Val Gln Val Gln
1               5                   10                  15

<210> SEQ ID NO 17
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 17

Tyr Gln Tyr Gln Tyr Gln Tyr Gln Tyr Gln Tyr Gln Tyr Gln Tyr Gln
1               5                   10                  15

<210> SEQ ID NO 18
<211> LENGTH: 16
<212> TYPE: PRT
<213> ORGANISM: Artificial
<220> FEATURE:
<223> OTHER INFORMATION: synthetic sequence designed for self assembly
```

<400> SEQUENCE: 18

His Gln His Gln His Gln His Gln His Gln His Gln His Gln His Gln
1               5                   10                  15

<210> SEQ ID NO 19
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 19

Ala Asn Ala Asn Ala Asn Ala Asn Ala Asn Ala Asn Ala Asn Ala Asn
1               5                   10                  15

<210> SEQ ID NO 20
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 20

Val Asn Val Asn Val Asn Val Asn Val Asn Val Asn Val Asn Val Asn
1               5                   10                  15

<210> SEQ ID NO 21
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 21

Tyr Asn Tyr Asn Tyr Asn Tyr Asn Tyr Asn Tyr Asn Tyr Asn Tyr Asn
1               5                   10                  15

<210> SEQ ID NO 22
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 22

His Asn His Asn His Asn His Asn His Asn His Asn His Asn His Asn
1               5                   10                  15

<210> SEQ ID NO 23
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 23

Ala Asn Ala Gln Ala Asn Ala Gln Ala Asn Ala Gln Ala Asn Ala Gln
1               5                   10                  15

<210> SEQ ID NO 24
<211> LENGTH: 16
<212> TYPE: PRT
<213> ORGANISM: Artificial
<220> FEATURE:
<223> OTHER INFORMATION: synthetic sequence designed for self assembly -continued

```
<400> SEQUENCE: 24

Ala Gln Ala Asn Ala Gln Ala Asn Ala Gln Ala Asn Ala Gln Ala Asn
1               5                   10                  15

<210> SEQ ID NO 25
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 25

Val Asn Val Gln Val Asn Val Gln Val Asn Val Gln Val Asn Val Gln
1               5                   10                  15

<210> SEQ ID NO 26
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 26

Val Gln Val Asn Val Gln Val Asn Val Gln Val Asn Val Gln Val Asn
1               5                   10                  15

<210> SEQ ID NO 27
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 27

Tyr Asn Tyr Gln Tyr Asn Tyr Gln Tyr Asn Tyr Gln Tyr Asn Tyr Gln
1               5                   10                  15

<210> SEQ ID NO 28
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 28

Tyr Gln Tyr Asn Tyr Gln Tyr Asn Tyr Gln Tyr Asn Tyr Gln Tyr Asn
1               5                   10                  15

<210> SEQ ID NO 29
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 29

His Asn His Gln His Asn His Gln His Asn His Gln His Asn His Gln
1               5                   10                  15

<210> SEQ ID NO 30
<211> LENGTH: 16
<212> TYPE: PRT
<213> ORGANISM: Artificial
<220> FEATURE:
<223> OTHER INFORMATION: synthetic sequence designed for self assembly
```

```
<400> SEQUENCE: 30

His Gln His Asn His Gln His Asn His Gln His Asn His Gln His Asn
1               5                   10                  15

<210> SEQ ID NO 31
<211> LENGTH: 18
<212> TYPE: PRT
<213> ORGANISM: Artificial
<220> FEATURE:
<223> OTHER INFORMATION: synthetic sequence designed for self assembly

<400> SEQUENCE: 31

Ala Lys Ala Gln Ala Asp Ala Lys Ala Gln Ala Asp Ala Lys Ala Gln
1               5                   10                  15

Ala Asp

<210> SEQ ID NO 32
<211> LENGTH: 18
<212> TYPE: PRT
<213> ORGANISM: Artificial
<220> FEATURE:
<223> OTHER INFORMATION: synthetic sequence designed for self assembly

<400> SEQUENCE: 32

Val Lys Val Gln Val Asp Val Lys Val Gln Val Asp Val Lys Val Gln
1               5                   10                  15

Val Asp

<210> SEQ ID NO 33
<211> LENGTH: 18
<212> TYPE: PRT
<213> ORGANISM: Artificial
<220> FEATURE:
<223> OTHER INFORMATION: synthetic sequence designed for self assembly

<400> SEQUENCE: 33

Tyr Lys Tyr Gln Tyr Asp Tyr Lys Tyr Gln Tyr Asp Tyr Lys Tyr Gln
1               5                   10                  15

Tyr Asp

<210> SEQ ID NO 34
<211> LENGTH: 18
<212> TYPE: PRT
<213> ORGANISM: Artificial
<220> FEATURE:
<223> OTHER INFORMATION: synthetic sequence designed for self assembly

<400> SEQUENCE: 34

His Lys His Gln His Asp His Lys His Gln His Asp His Lys His Gln
1               5                   10                  15

His Asp

<210> SEQ ID NO 35
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 35

Arg Ala Arg Ala Asp Ala Asp Ala Arg Ala Arg Ala Asp Ala Asp Ala
1               5                   10                  15
```

```
<210> SEQ ID NO 36
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 36

Arg Ala Asp Ala Arg Gly Asp Ala Arg Ala Asp Ala Arg Gly Asp Ala
1               5                   10                  15

<210> SEQ ID NO 37
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 37

Arg Ala Glu Ala Arg Ala Glu Ala Arg Ala Glu Ala Arg Ala Glu Ala
1               5                   10                  15

<210> SEQ ID NO 38
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 38

Lys Ala Asp Ala Lys Ala Asp Ala Lys Ala Asp Ala Lys Ala Asp Ala
1               5                   10                  15

<210> SEQ ID NO 39
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 39

Ala Glu Ala Glu Ala His Ala His Ala Glu Ala Glu Ala His Ala His
1               5                   10                  15

<210> SEQ ID NO 40
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 40

Phe Glu Phe Glu Phe Lys Phe Lys Phe Glu Phe Glu Phe Lys Phe Lys
1               5                   10                  15

<210> SEQ ID NO 41
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 41

Leu Glu Leu Glu Leu Lys Leu Lys Leu Glu Leu Glu Leu Lys Leu Lys
1               5                   10                  15
```

```
<210> SEQ ID NO 42
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 42

Ala Glu Ala Glu Ala Lys Ala Lys Ala Glu Ala Glu Ala Lys Ala Lys
1               5                   10                  15

<210> SEQ ID NO 43
<211> LENGTH: 12
<212> TYPE: PRT
<213> ORGANISM: Artificial
<220> FEATURE:
<223> OTHER INFORMATION: synthetic sequence designed for self assembly

<400> SEQUENCE: 43

Ala Glu Ala Glu Ala Glu Ala Glu Ala Lys Ala Lys
1               5                   10

<210> SEQ ID NO 44
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 44

Lys Ala Lys Ala Lys Ala Lys Ala Glu Ala Glu Ala Glu Ala Glu Ala
1               5                   10                  15

<210> SEQ ID NO 45
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 45

Ala Glu Ala Glu Ala Glu Ala Glu Ala Lys Ala Lys Ala Lys Ala Lys
1               5                   10                  15

<210> SEQ ID NO 46
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 46

Arg Ala Arg Ala Arg Ala Arg Ala Asp Ala Asp Ala Asp Ala Asp Ala
1               5                   10                  15

<210> SEQ ID NO 47
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 47

Ala Asp Ala Asp Ala Asp Ala Asp Ala Arg Ala Arg Ala Arg Ala Arg
1               5                   10                  15
```

```
<210> SEQ ID NO 48
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 48

Asp Ala Asp Ala Asp Ala Asp Ala Arg Ala Arg Ala Arg Ala Arg Ala
1               5                   10                  15

<210> SEQ ID NO 49
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 49

His Glu His Glu His Lys His Lys His Glu His Glu His Lys His Lys
1               5                   10                  15

<210> SEQ ID NO 50
<211> LENGTH: 20
<212> TYPE: PRT
<213> ORGANISM: Artificial
<220> FEATURE:
<223> OTHER INFORMATION: synthetic sequence designed for self assembly

<400> SEQUENCE: 50

Val Glu Val Glu Val Glu Val Glu Val Glu Val Glu Val Glu Val Glu
1               5                   10                  15

Val Glu Val Glu
            20

<210> SEQ ID NO 51
<211> LENGTH: 20
<212> TYPE: PRT
<213> ORGANISM: Artificial
<220> FEATURE:
<223> OTHER INFORMATION: synthetic sequence designed for self assembly

<400> SEQUENCE: 51

Arg Phe Arg Phe Arg Phe Arg Phe Arg Phe Arg Phe Arg Phe Arg Phe
1               5                   10                  15

Arg Phe Arg Phe
            20

<210> SEQ ID NO 52
<211> LENGTH: 68
<212> TYPE: PRT
<213> ORGANISM: Homo sapiens

<400> SEQUENCE: 52

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
            35                  40                  45

Val Cys Ile Asp Pro Lys Leu Lys Trp Ile Gln Glu Tyr Leu Glu Lys
        50                  55                  60

Ala Leu Asn Lys
65
```

```
<210> SEQ ID NO 53
<211> LENGTH: 68
<212> TYPE: PRT
<213> ORGANISM: Homo sapiens
<220> FEATURE:
<221> NAME/KEY: misc_feature
<222> LOCATION: (4)..(4)
<223> OTHER INFORMATION: X is ala, arg, asx, cys, glx, gly, his, ile,
      leu, lys, met, phe, pro, thr, trp, tyr, or val

<400> SEQUENCE: 53

Lys Pro Val Xaa Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 54
<211> LENGTH: 68
<212> TYPE: PRT
<213> ORGANISM: Homo sapiens

<400> SEQUENCE: 54

Lys Pro Val Val Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 55
<211> LENGTH: 68
<212> TYPE: PRT
<213> ORGANISM: Homo sapiens
<220> FEATURE:
<221> NAME/KEY: misc_feature
<222> LOCATION: (5)..(5)
<223> OTHER INFORMATION: X is ala, arg, asx, cys, gln, gly, his, ile,
      lys, met, phe, pro, ser, thr, tyr, or val

<400> SEQUENCE: 55

Lys Pro Val Ser Xaa Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65
```

```
<210> SEQ ID NO 56
<211> LENGTH: 68
<212> TYPE: PRT
<213> ORGANISM: Homo sapiens

<400> SEQUENCE: 56

Lys Pro Val Ser Pro Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 57
<211> LENGTH: 6
<212> TYPE: PRT
<213> ORGANISM: Homo sapiens

<400> SEQUENCE: 57

Gly Gly Gly Gly Gly Gly
1               5

<210> SEQ ID NO 58
<211> LENGTH: 6
<212> TYPE: PRT
<213> ORGANISM: Homo sapiens

<400> SEQUENCE: 58

Gly Ile Val Gly Pro Leu
1               5

<210> SEQ ID NO 59
<211> LENGTH: 6
<212> TYPE: PRT
<213> ORGANISM: Homo sapiens

<400> SEQUENCE: 59

Pro Val Gly Leu Ile Gly
1               5

<210> SEQ ID NO 60
<211> LENGTH: 204
<212> TYPE: DNA
<213> ORGANISM: Homo sapiens

<400> SEQUENCE: 60
aagcccgtcg tcctgagcta cagatgccca tgccgattct tcgaaagcca tgttgccaga      60
gccaacgtca agcatctcaa aattctcaac actccaaact gtgcccttca gattgtagcc     120
cggctgaaga caacaacag acaagtgtgc attgacccga agctaaagtg gattcaggag      180
tacctggaga aagcttttaaa caag                                           204

<210> SEQ ID NO 61
<211> LENGTH: 273
<212> TYPE: DNA
<213> ORGANISM: Homo sapiens
```

```
<400> SEQUENCE: 61
aagcccgtcg tcctgagcta cagatgccca tgccgattct tcgaaagcca tgttgccaga      60
gccaacgtca agcatctcaa aattctcaac actccaaact gtgcccttca gattgtagcc     120
cggctgaaga acaacaacag acaagtgtgc attgacccga agctaaagtg gattcaggag     180
tacctggaga aagctttaaa caagtgagga atcgtgggac ctctgcgtgc ccgtgccgac     240
gccgacgccc gtgcccgtgc cgacgccgac gcc                                  273

<210> SEQ ID NO 62
<211> LENGTH: 269
<212> TYPE: DNA
<213> ORGANISM: Homo sapiens

<400> SEQUENCE: 62
aagcccgtcg tcctgagcta cagatgccca tgccgattct tcgaaagcca tgttgccaga      60
gccaacgtca agcatctcaa aattctcaac actccaaact gtgcccttca gattgtagcc     120
cggctgaaga acaacaacag acaagtgtgc attgacccga agctaaagtg gattcaggag     180
tacctggaga aagctttaaa caagcctgtg ggactgatcg gagtgcccgt gccgacgccg     240
acgcccgtgc ccgtgccgac gccgacgcc                                       269

<210> SEQ ID NO 63
<211> LENGTH: 270
<212> TYPE: DNA
<213> ORGANISM: Homo sapiens

<400> SEQUENCE: 63
aagcccgtcg tcctgagcta cagatgccca tgccgattct tcgaaagcca tgttgccaga      60
gccaacgtca agcatctcaa aattctcaac actccaaact gtgcccttca gattgtagcc     120
cggctgaaga acaacaacag acaagtgtgc attgacccga agctaaagtg gattcaggag     180
tacctggaga aagctttaaa caagggaggc gggggaggtg ggcgtgcccg tgccgacgcc     240
gacgcccgtg cccgtgccga cgccgacgcc                                      270

<210> SEQ ID NO 64
<211> LENGTH: 17
<212> TYPE: PRT
<213> ORGANISM: Homo sapiens

<400> SEQUENCE: 64

Lys Pro Val Ser Leu Ser Tyr Arg Cys Pro Cys Arg Phe Phe Glu Ser
1               5                   10                  15

His

<210> SEQ ID NO 65
<211> LENGTH: 17
<212> TYPE: PRT
<213> ORGANISM: Homo sapiens

<400> SEQUENCE: 65

Lys Pro Val Val Leu Ser Tyr Arg Cys Pro Cys Arg Phe Phe Glu Ser
1               5                   10                  15

His

<210> SEQ ID NO 66
<211> LENGTH: 17
<212> TYPE: PRT
<213> ORGANISM: Homo sapiens
```

-continued

```
<400> SEQUENCE: 66

Lys Pro Val Ser Pro Ser Tyr Arg Cys Pro Cys Arg Phe Phe Glu Ser
1               5                   10                  15
His
```